US00PP26758P2

(12) United States Plant Patent
Larsen

(10) Patent No.: US PP26,758 P2
(45) Date of Patent: May 24, 2016

(54) ***OSTEOSPERMUM* PLANT NAMED 'SUNOST1401'**

(50) Latin Name: *Osteospermum ecklonis*
Varietal Denomination: Sunost1401

(71) Applicant: Bjarne Nyholm Larsen, Odense N. (DK)

(72) Inventor: Bjarne Nyholm Larsen, Odense N. (DK)

(73) Assignee: Sunny Gronnegyden APS, Odense N. (DK)

( * ) Notice: Subject to any disclaimer, the term of this patent is extended or adjusted under 35 U.S.C. 154(b) by 58 days.

(21) Appl. No.: 14/121,240

(22) Filed: Aug. 14, 2014

(51) Int. Cl.
*A01H 5/00* (2006.01)

(52) U.S. Cl.
USPC ..... Plt./360

(58) Field of Classification Search
USPC ..... Plt./360
See application file for complete search history.

(56) References Cited

PUBLICATIONS

PLUTO Plant Variety Database Dec. 10, 2015. p. 1.*

* cited by examiner

*Primary Examiner* — Annette Para
(74) *Attorney, Agent, or Firm* — C. A. Whealy

(57) ABSTRACT

A new and distinct cultivar of *Osteospermum* plant named 'Sunost1401', characterized by its compact, upright, outwardly spreading and mounding plant habit; freely branching growth habit; freely flowering habit; large daisy-type inflorescences with velvety dark purple-colored ray florets; and good garden performance.

2 Drawing Sheets

Botanical designation: *Osteospermum ecklonis.*
Cultivar denomination: 'SUNOST1401'.

BACKGROUND OF THE INVENTION

The present invention relates to a new and distinct cultivar of *Osteospermum* plant, botanically known as *Osteospermum ecklonis* and hereinafter referred to by the name 'Sunost1401'.

The new *Osteospermum* plant is a product of a planned breeding program conducted by the Inventor in Odense, Denmark. The objective of the program is to create and develop new *Osteospermum* plants with compact and uniformly mounded plant habit, freely flowering habit and attractive ray and disc floret coloration.

The new *Osteospermum* plant originated from a cross-pollination by the Inventor in May, 2010 of *Osteospermum ecklonis* 'Sunny Carlos', disclosed in U.S. Plant Pat. No. 19,637, as the female, or seed, parent with a proprietary selection of *Osteospermum ecklonis* identified as code number 08.50.010, not patented, as the male, or pollen, parent. The new *Osteospermum* plant was discovered and selected by the Inventor as a single flowering plant within the progeny of the stated cross-pollination in a controlled greenhouse environment in Odense, Denmark in June, 2011.

Asexual reproduction of the new *Osteospermum* plant by terminal cuttings in a controlled greenhouse environment in Odense, Denmark since September, 2011 has shown that the unique features of this new *Osteospermum* plant are stable and reproduced true to type in successive generations.

SUMMARY OF THE INVENTION

Plants of the new *Osteospermum* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'Sunost1401'. These characteristics in combination distinguish 'Sunost1401' as a new and distinct *Osteospermum* plant:

1. Compact, upright, outwardly spreading and mounding plant habit.
2. Freely branching growth habit.
3. Freely flowering habit.
4. Large daisy-type inflorescences with velvety dark purple-colored ray florets.
5. Good garden performance.

Plants of the new *Osteospermum* differ primarily from plants of the female parent, 'Sunny Carlos', in the following characteristics:

1. Plants of the new *Osteospermum* are more compact than plants of 'Sunny Carlos'.
2. Plants of the new *Osteospermum* and 'Sunny Carlos' differ in ray floret color as plants of 'Sunny Carlos' have white-colored ray florets.

Plants of the new *Osteospermum* differ primarily from plants of the male parent selection in the following characteristics:

1. Plants of the new *Osteospermum* are more compact than plants of the male parent selection.
2. Plants of the new *Osteospermum* and the male parent selection differ in ray floret color as plants of the male parent selection have pale purple-colored ray florets.

Plants of the new *Osteospermum* can be compared to plants of the *Osteospermum ecklonis* 'Sunny Mary', disclosed in U.S. Plant Pat. No. 16,389. In side-by-side comparisons conducted in Odense, Denmark, plants of the new *Osteospermum* differed from plants of 'Sunny Mary' in the following characteristics:

1. Plants of the new *Osteospermum* and 'Sunny Mary' differed in leaf shape.
2. Plants of the new *Osteospermum* had larger inflorescences than plants of 'Sunny Mary'.
3. Plants of the new *Osteospermum* and 'Sunny Mary' differed in ray floret color as plants of 'Sunny Mary' had red purple-colored ray florets.

BRIEF DESCRIPTION OF THE PHOTOGRAPHS

The accompanying photographs illustrate the overall appearance of the new *Osteospermum* plant showing the colors as true as it is reasonably possible to obtain in colored reproductions of this type. Colors in the photographs may differ slightly from the color values cited in the detailed botanical description which accurately describe the colors of the new *Osteospermum* plant.

The photograph on the first sheet comprises a side perspective view of a typical flowering plant of 'Sunost1401' grown in a container.

The photograph on the second sheet is a close-up view of a typical inflorescence of 'Sunost1401'.

DETAILED BOTANICAL DESCRIPTION

The aforementioned photographs, following observations and measurements describe plants grown during the winter in 11-cm containers in a glass-covered greenhouse in Odense, Denmark and under cultural practices typical of commercial *Osteospermum* production. During the production of the plants, day temperatures ranged from 14° C. to 20° C. and night temperatures averaged 14° C. Plants were pinched one time and were 14 weeks old when the photographs and description were taken. In the following description, color references are made to The Royal Horticultural Society Colour Chart, 2007 Edition, except where general terms of ordinary dictionary significance are used.

Botanical classification: *Osteospermum ecklonis* 'Sunost1401'.

Parentage:

*Female, or seed, parent.*—*Osteospermum ecklonis* 'Sunny Carlos', disclosed in U.S. Plant Pat. No. 19,637.

*Male, or pollen, parent.*—Proprietary selection of *Osteospermum ecklonis* identified as code number 08.50.010, not patented.

Propagation:

*Type.*—Terminal vegetative cuttings.

*Time to initiate roots, summer.*—About twelve days at temperatures about 18° C.

*Time to initiate roots, winter.*—About 14 days at temperatures about 18° C. to 20° C.

*Time to produce a rooted cutting, summer.*—About 20 days at temperatures about 18° C. to 20° C.

*Time to produce a rooted cutting, winter.*—About 28 days at temperatures about 18° C.

*Root description.*—Medium in thickness, fibrous; white in color.

*Rooting habit.*—Freely branching; medium density.

Plant description:

*Plant and growth habit.*—Compact, upright, outwardly spreading and mounding plant habit; inflorescences positioned above and beyond the foliar plane on strong peduncles; moderately vigorous growth habit.

*Plant height.*—About 14.5 cm.

*Plant diameter.*—About 20.3 cm.

*Lateral branches.*—Quantity per plant: Freely branching habit with about five primary lateral branches per plant; pinching enhances branching potential. Length: About 6.3 cm. Diameter: About 5 mm. Internode length: About 3 mm. Strength: Strong. Texture: Smooth, glabrous. Color: Close to 144B to 144C.

*Leaf description.*—Arrangement: Alternate, simple. Length: About 4.7 cm. Width: About 4.4 cm. Shape: Obovate. Apex: Rounded. Base: Short attenuate. Margin: Irregularly and coarsely crenate. Texture, upper and lower surfaces: Sparsely to moderately glandular pubescence; rough. Venation pattern: Pinnate, arcuate. Color: Developing leaves, upper surface: Close to 137A. Developing leaves, lower surface: Close to 137D. Fully expanded leaves, upper surface: Darker than between 147A and N189A; venation, close to 144B. Fully expanded leaves, lower surface: Close to 137A to 137B; venation, close to 144C. Petioles: Length: About 1.8 cm. Diameter: About 3 mm to 4.5 mm. Color, upper and lower surfaces: Close to 144C.

Inflorescence description:

*Appearance.*—Daisy-type inflorescence form with oblanceolate to narrowly oblong-shaped ray florets; inflorescences terminal and axillary and positioned above and beyond the foliar plane on strong peduncles; disc and ray florets developing acropetally on a capitulum; inflorescences face mostly upright to slightly outwardly.

*Flowering habit.*—Freely flowering habit with about 50 inflorescences developing per plant.

*Fragrance.*—None detected.

*Flowering response.*—In Denmark, plants of the new *Osteospermum* flower continuously from spring to late summer; early flowering habit, plants begin flowering about six to eight weeks after pinching.

*Inflorescence longevity.*—Inflorescences of plants of the new *Osteospermum* last about two to three weeks on the plant; inflorescences not persistent.

*Inflorescence buds.*—Height: About 1.4 cm. Diameter: About 1.1 cm. Shape: Ovate. Color: Close to 137C; towards the apex, close to N186C.

*Inflorescence size.*—Diameter: About 5.8 cm. Depth (height): About 1.6 cm. Disc diameter: About 1.5 cm. Receptacle diameter: About 4 mm. Receptacle height: About 2 mm.

*Ray florets.*—Length: About 2.9 cm. Width: About 9 mm. Shape: Oblanceolate to narrowly oblong; reflexing with development. Apex: Emarginate. Base: Attenuate. Margin: Entire. Texture, upper surface: Smooth, glabrous; velvety. Texture, lower surface: Mostly smooth, glabrous; towards the base, pubescent. Number of ray florets per inflorescence: About 26 arranged in two whorls. Color: When opening, upper surface: Close to N79B to N79C. When opening, lower surface: Close to N79A to N79B. Fully opened, upper surface: Close to N79B to N79C; color becoming closer to between N186B and 187A with development. Fully opened, lower surface: Close to N79B to N79C; stripes, close to 71A.

*Disc florets.*—Shape: Tubular; apex dentate, five-pointed. Length: About 8 mm. Diameter, apex: About 3 mm. Diameter, base: About 1 mm. Number of disc florets per inflorescence: About 150. Color, immature: Apex: Close to N79A to N79B. Mid-section: Close to 186A. Base: Close to 186D. Color, mature: Apex: Close to N79B to N79C. Mid-section: Close to 79D. Base: Close to 186C.

*Phyllaries*.—Quantity per inflorescence: About 28 arranged in two whorls. Length: About 1 cm. Width: About 2 mm. Shape: Lanceolate. Apex: Narrowly acute. Base: Cuneate. Margin: Entire. Texture, upper surface: Smooth, glabrous. Texture, lower surface: Sparsely pubescent. Color, upper surface: Close to 147B; margins, close to 147D. Color, lower surface: Close to 137B; margins, close to 137D.

*Peduncles*.—Length, terminal peduncle: About 7.1 cm. Length, fourth peduncle: About 4.3 cm. Diameter: About 2.5 mm. Strength: Strong. Aspect, terminal peduncles: Mostly upright. Aspect, axillary peduncles: About 32.5° from stem axis. Texture: Moderately pubescent. Color: Close to 143A.

*Reproductive organs*.—Androecium: Present on disc florets only. Filament length: About 2 mm. Anther shape: Lanceolate. Anther length: About 4 mm. Anther color: Close to 203B. Pollen amount: Abundant. Pollen color: Close to 24A. Gynoecium: Present on both ray and disc florets. Pistil length: About 7 mm. Stigma shape: Bi-parted. Stigma color: Close to N186C. Style length: About 6.5 mm. Style color: Close to N79C. Ovary color: Close to 144D.

*Seeds and fruits*.—Seed and fruit development has not been observed on plants of the new *Osteospermum*.

Disease & pest resistance: Plants of the new *Osteospermum* have not been shown to be resistant to pathogens and pests common to *Osteospermum* plants.

Garden performance: Plants of the new *Osteospermum* have been observed to have good garden performance and to tolerate rain, wind, high temperatures about 40° C. and to be hardy to USDA Hardiness Zone 9.

It is claimed:

1. A new and distinct *Osteospermum* plant named 'Sunost1401' as illustrated and described.

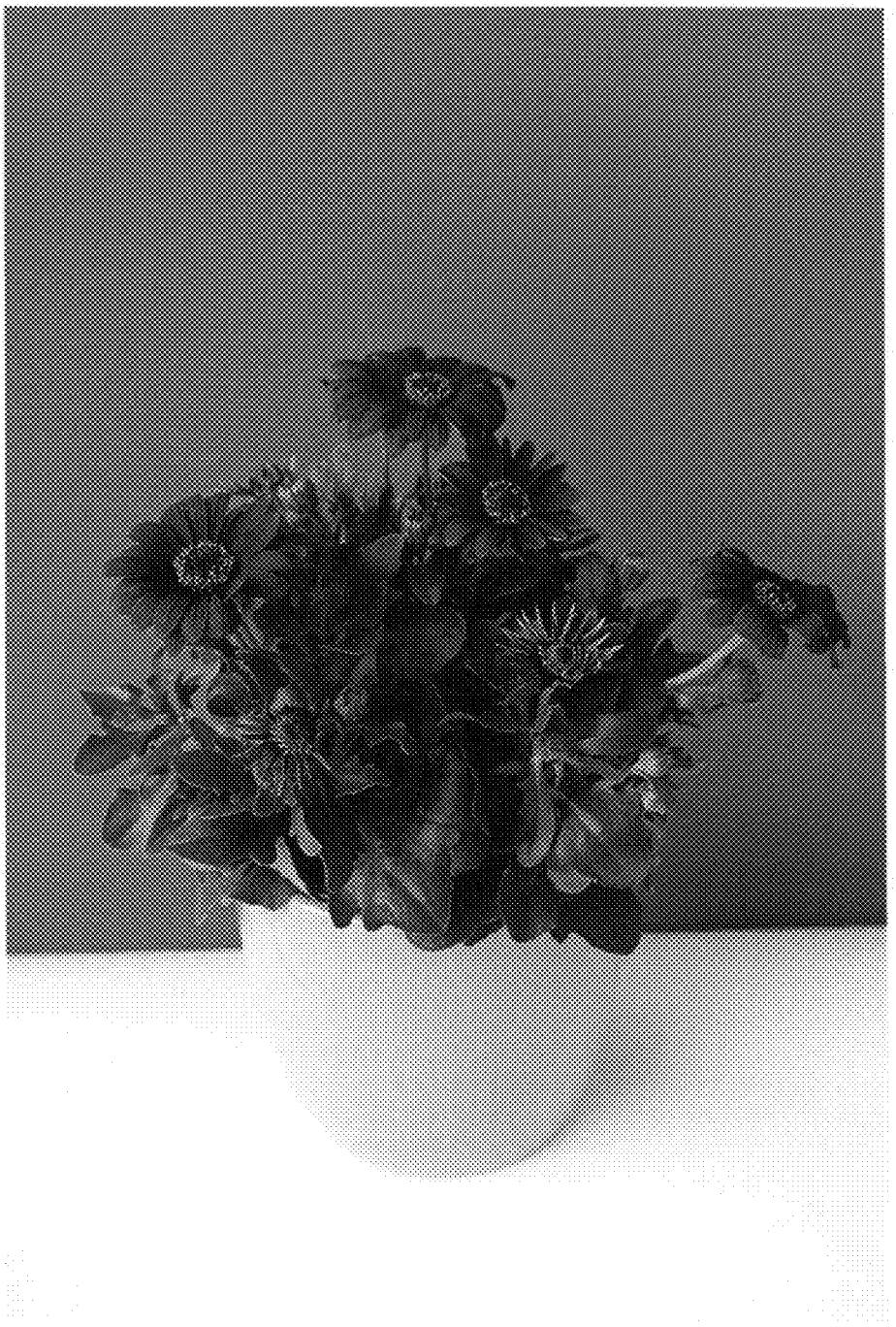

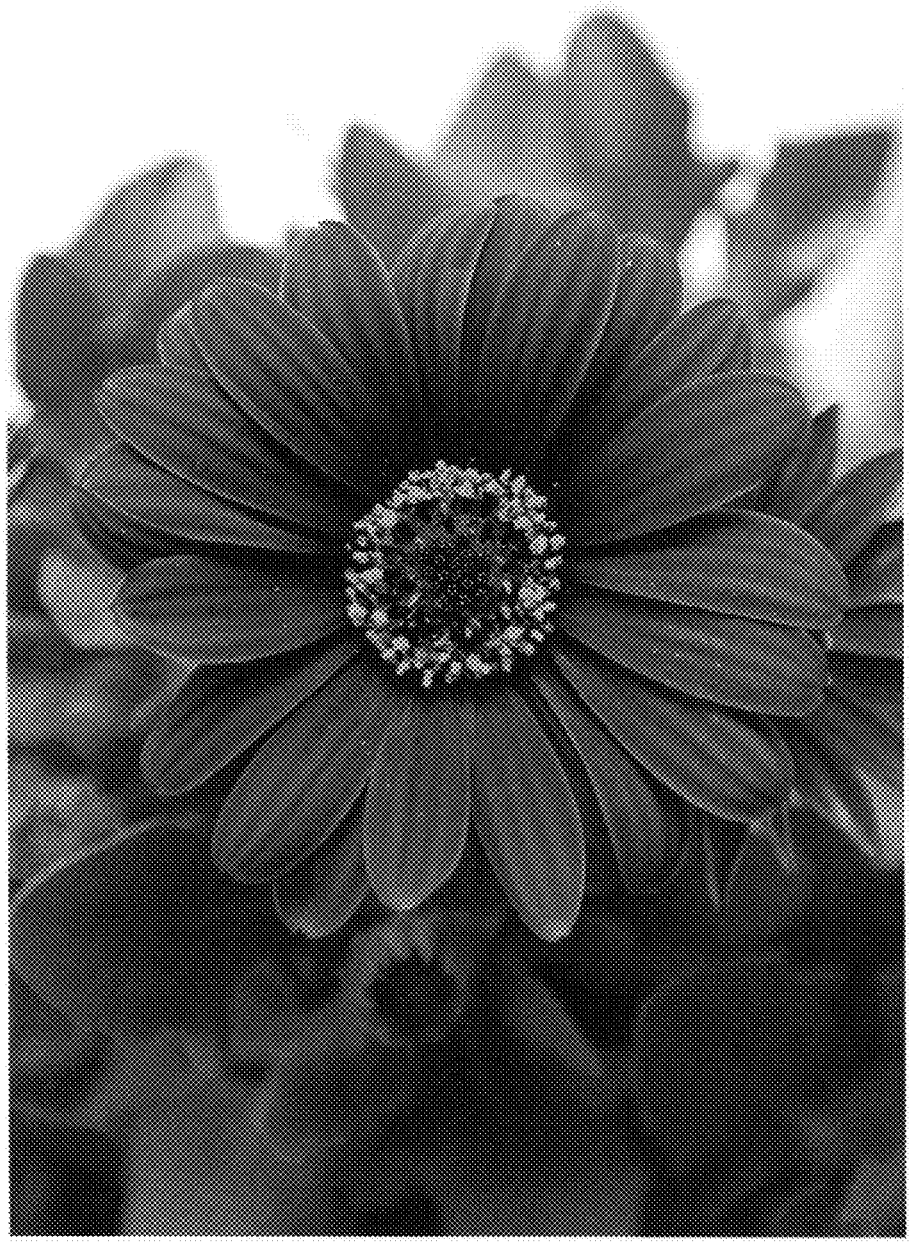

* * * * *